United States Patent [19]

Tsubota et al.

[11] Patent Number: 4,990,150
[45] Date of Patent: Feb. 5, 1991

[54] BANDAGE FOR MAINTAINING ANTERIOR CHAMBER OF EYE

[75] Inventors: Kazuo Tsubota, Utsunomiya; Hiroshi Sakai, Kodaira, both of Japan

[73] Assignee: Hoya Corporation, Tokyo, Japan

[21] Appl. No.: 376,580

[22] Filed: Jul. 7, 1989

[51] Int. Cl.⁵ .............................................. A01F 9/00
[52] U.S. Cl. ......................................... 606/107; 623/4
[58] Field of Search ...................... 128/163, 858; 623/4, 623/5, 6; 606/107, 166; 604/294, 297, 298, 300

[56] References Cited

U.S. PATENT DOCUMENTS

| Re. 28,873 | 6/1976 | Morgan | 604/298 |
| 4,406,285 | 9/1983 | Villasenor et al. | 606/166 |
| 4,810,082 | 3/1989 | Abel, Jr. | 623/5 |

FOREIGN PATENT DOCUMENTS 63-9797 8/1989 Japan .
1012915 4/1983 U.S.S.R. ............... 604/294

OTHER PUBLICATIONS

Tsubota "An Aspiration-Irrigation Soft Contact Lens for Maintenance of the Anterior Chamber" American Journal of Ophthalmology, vol. 106, Dec. 15, 1988 pp. 759-760.

Primary Examiner—Ronald Frinks
Attorney, Agent, or Firm—Nixon & Vanderhye

[57] ABSTRACT

The bandage for maintaining the anterior chamber of an eye according to the present invention is formed so as to cover an incision during operation and to tightly contact with the incision and its circumference, has a small hole for insertion of instruments for operation and is transparent. This bandage can prevent the outflow of aqueous humor through an incision during ocular operation without conducting the temporary suture of incision and thereby enables ocular operation in a state where the anterior chamber is maintained. Therefore, the bandage has solved various problems (e.g. complicated operation procedure, long operation time, high invasion associated with operation) encountered in the conventional ocular operation wherein the incision is temporarily sutured to prevent the outflow of aqueous humor therethrough and thereby to maintain the anterior chamber.

9 Claims, 2 Drawing Sheets

BANDAGE FOR MAINTAINING ANTERIOR CHAMBER OF EYE

BACKGROUND OF THE INVENTION

1. Field of the Invention

The present invention relates to a bandage for maintaining the anterior chamber of an eye, used in ocular operations.

2. Description of the Prior Art

Ophthalmic operations such as extraction of cataract, iridectomy, implantation of intraocular lens and the like comprise forming an incision in the cornea, sclera, conjunctiva, etc. of an eye, inserting instruments for operation into the eye through the incision and conducting a required operation inside the eye. If the aqueous humor filling the anterior chamber of eye flows out of the chamber during the operation, the anterior chamber shrinks and transforms, which invites the contact of other tissues and instruments for operation to the corneal endothelium. The cells of the corneal endothelium, unlike ordinary cells, make no cell division. If there occurs the above-mentioned contact, the portions of the endothelial cells which have received the contact are damaged. The damage is restored to some extent by the expansion of the cells of the endothelium surrounding the damaged portions; however, when the damaged portions are large, the restoration has a limit. When the damage is beyond the limit, the aqueous humor is taken into the corneal stroma inviting edema and impairing the transparency of the cornea. Thus, in ocular operation, it is necessary to maintain the anterior chamber so that there occurs no contact of other tissues and instruments for operation to the corneal endothelium. To achieve this, a measure must be taken to prevent the outflow of aqueous humor.

Ocular operations have conventionally been conducted by subjecting an incision to temporary suture to prevent the outflow of aqueous humor and then inserting instruments for operation into an eye through a small space formed after the temporary suture. After the completion of the operation, the temporary suture is untied and a final suture is made. Therefore, the conventional operation has had problems of complicated operation procedures, long operation time and high invasion associated with the operation.

SUMMARY OF THE INVENTION

The present invention has been made in order to solve the above-mentioned problems of conventional ocular operations.

An object of the present invention is to provide a bandage for maintaining the anterior chamber of an eye, which enables the performance of ocular operations without conducting the temporary suture of incision.

Other objects of the present invention will become apparent from the following description.

According to the present invention, there is provided a bandage for maintaining the anterior chamber of an eye, which is formed so as to cover an incision during operation and to tightly contact with the incision and its circumference, which has a small hole for insertion of instruments for operation, and which is transparent.

The bandage for maintaining the anterior chamber of an eye according to the present invention can prevent the outflow of aqueous humor through an incision by covering the incision and enables the insertion of instruments for operation into an eye through the small hole provided in the bandage. Therefore, the bandage can maintain the anterior chamber and enables the performance of ocular operations without conducting the temporary suture of incision.

DETAILED DESCRIPTION OF THE INVENTION

The preferred embodiments of the present invention are explained in detail below referring to the accompanying drawings.

Figure 1A:
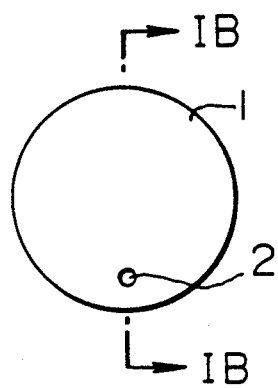
FIG. 1A is a frontal view of a bandage for maintaining the anterior chamber of an eye according to an embodiment of the present invention.
Figure 1B:
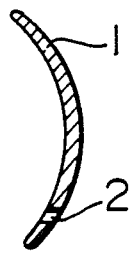
FIG. 1B is a sectional view of the bandage of FIG. 1A, taken along the line IB—IB of FIG. 1A.

The bandage 1 for maintaining the anterior chamber of an eye, according to a preferred embodiment of the present invention shown in FIGS. 1A and 1B has a circular or oval shape overall and a curved section for tightly contacting the outer front surface of the eye and an incision therethrough into the anterior chamber. A small circular hole 2 preferably having a diameter of 1–3 mm is formed from the anterior surface to the posterior surface of the bandage 1 at an appropriate position inside the peripheral edge of the bandage 1 to allow the insertion of instruments for operation such as pincette, hook, forceps, scalpel, surgical knife, irrigator, aspirator and the like. The bandage 1 is made of a material which is transparent to allow the observation of the actual condition of an operation conducted inside the eye and which is elastic to allow its tight contact with the cornea, sclera, conjunctiva, etc. Preferably, the material of the bandage 1 further has such properties as to give no adverse effect on the aqueous humor and the eye portions to which the bandage makes direct contact, such as cornea, sclera, conjunctiva and the like, and also has such softness as to give no injury to said eye portions. Therefore, specific examples of the suitable material of the bandage 1 include a hydrogel consisting of a hydroxyethyl methacrylate homopolymer or a copolymer of hydroxyethyl methacrylate and other monomer (e.g. alkyl (meth)acrylate such as methyl methacrylate or the like), a hydrogel consisting of a copolymer of vinyl pyrrolidone and other monomer (e.g. alkyl (meth)acrylate such as methyl methacrylate or the like), a hydrogel consisting of a polyvinyl alcohol type polymer, a silicone rubber, a butyl rubber, etc. The dimensions of the bandage 1 are, for example, 10–20 mm$\phi$, particularly about 16 mm$\phi$ in diameter and 0.2–0.5 mm, particularly about 0.4 mm in thickness.

Figure 2A:
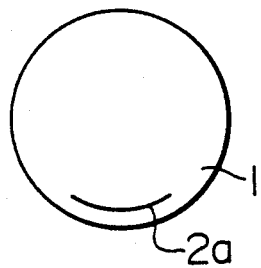
FIGS. 2A, 2B and 2C are each a view of a bandage with a modified small hole according to the present invention.
Figure 2B:
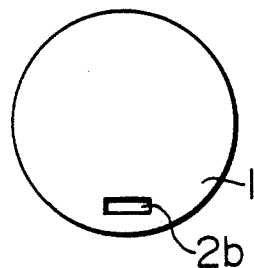
Figure 2C:
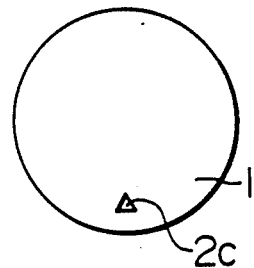

FIGS. 2A, 2B and 2C each show a bandage 1 with a modified small hole 2a, 2b or 2c according to the present invention. In these figures, the overall shape of the bandage 1 is shown to be a circle as an example. The small hole 2a of FIG. 2A is formed to be a line, the length of which is preferably 5-10 mm. This may be a curved or straight line. The small hole 2b of FIG. 2B is a rectangle, the long and short sides of which are preferably 4-8 mm and 1-3 mm long, respectively. The small hole 2c of FIG. 2C is a triangle, the three sides of which are preferably 1-5 mm long. The small hole of the bandage 1 is appropriately determined depending upon the instruments for operation to be inserted therethrough, and may take a shape and dimensions other than mentioned above.

Figure 3A:
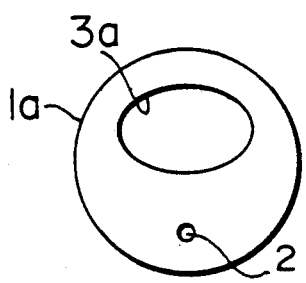
FIGS. 3A, 3B and 3C are each a view of a bandage with a modified overall shape according to the present invention.
Figure 3B:
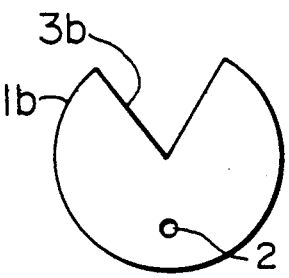
Figure 3C:
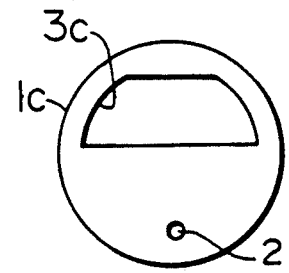

FIGS. 3A, 3B and 3C each show a bandage 1a, 1b or 1c with a modified overall shape according to the present invention. In these figures, the small hole 2 is shown to be a small circle as an example. In the bandage 1a of FIG. 3A, a circular large opening or an oval large opening 3a (preferable length of major axis = 5-10 mm, preferable length of minor axis = 3-7 mm) is formed; in the bandage 1b of FIG. 3B, a fan-shaped cut-out 3b (preferable cut-out angle = 10-80°) is formed; and in the bandage 1c of FIG. 3C, a trapezoidal or generally trapezoidal large opening 3c is formed, the short upper side, the long lower side and the height of which are preferably 5-7.5 mm, 10-15 mm and 2.5-7.5 mm, respectively. The formation of large opening 3a or 3c or cut-out 3b facilitates the observation of anterior chamber. The large opening 3a or 3c or cut-out 3b also serves to remove the bubbles entering between the cornea and the bandage. Incidentally, these bubbles enter between the cornea and the bandage during the handling of instruments for operation and make the inside of eye less visible. The large opening 3a or 3c or cut-out 3b further enables oxygen supply to the cornea therethrough. The large opening 3a or 3c or cut-out 3b may have a shape or dimensions other than mentioned above, and the number may be one or more.

Figure 4:
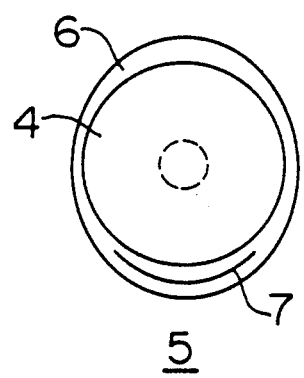
FIG. 4 is a frontal view of the cornea, sclera and limbus showing the position of an incision formed during eye operation.
Figure 5:
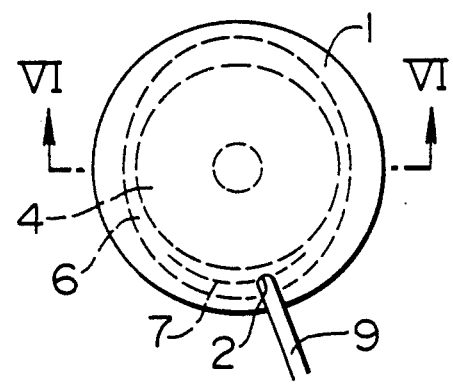
FIG. 5 is a frontal view of an eye to which a bandage of the present invention has been applied.
Figure 6:
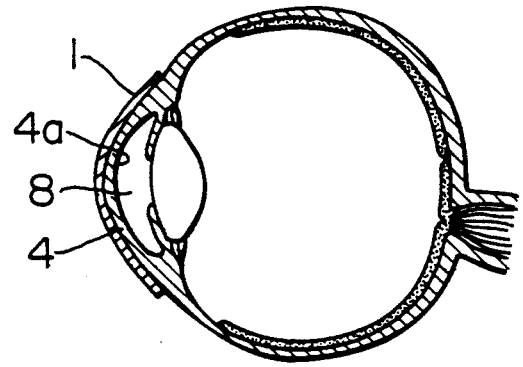
FIG. 6 is a horizontal sectional view of the eye and bandage of FIG. 5, taken along the line VI—VI of FIG. 5.

Next, there is explained a case in which the bandage 1 for maintaining the anterior chamber of an eye, shown in FIG. 1 is used in an operation for implantation of intraocular lens. In this operation, as shown in FIG. 4, firstly there is formed an incision 7 in the limbus 6 between the cornea 4 and the sclera 5. Next, a lens nucleus (diameter: about 10 mmφ) not shown is extracted out of the eye through the incision 7. Incidentally, the length of the incision 7 is, for example, about 12-18 mm. The incision 7 is not subjected to temporary suture as done conventionally, but instead a bandage 1 for maintaining the anterior chamber of an eye according to the present invention is applied (see FIGS. 5 and 6). The bandage 1 is applied so as to cover the incision 7, whereby the outflow of the aqueous humor in the anterior chamber 8 is prevented and the shape of the anterior chaber 8 is maintained. Next, an irrigator 9 is inserted through a small hole 2 and sucks the cortex, etc. remaining in the crystalline capsule in the anterior chamber 8. During this operation procedure, the shape of the anterior chamber is maintained as mentioned above; therefore, there occurs no contact of the irrigator 9 to the endothelium 4a of the cornea 4, or of the endothelium 4a to other tissues and accordingly the endothelium 4a undergoes neither destruction nor damage. Since the bandage 1 is transparent, it is easy to observe the actual condition of the operation conducted in the eye. After the residual cortex has been sucked, the bandage 1 is removed and an intraocular lens (diameter: about 6 mmφ) is inserted. Then, the bandage 1 is reapplied; an instrument 9 for positioning of intraocular lens is inserted through the small hole 2 to fix the intraocular lens at a given position; the bandage 1 is removed; and lastly the incision 7 is sutured. Incidentally, during the operation, the bandage 1 which is first used can be changed to the other bandage having a different small hole more suitable for other instrument for operation.

As described above, the bandage for maintaining the anterior chamber of an eye according to the present invention can prevent the outflow of aqueous humor through an incision by covering the incision and enables the insertion of instruments for operation into an eye through the small hole formed in the bandage. Therefore, the bandage enables eye operation while maintaining the anterior chamber. Consequently, by using the bandage of the present invention, there is required neither temporary suture of incision nor removal of the stitches as conducted conventionally. As a result, eye operation becomes simpler and operation time becomes shorter. Moreover, since the bandage is transparent, it is easy to observe the actual condition of the operation conducted in the eye.

What is claimed is:

1. A bandage having anterior and posterior surfaces and a peripheral edge for maintaining the anterior chamber of an eye during an opthalmic operation, which is formed so as to cover the outer front surface of the eye and an incision therethrough during said operation and to tightly contact the incision and its circumference so as to prevent the outflow of aqueous humor from the anterior chamber, said bandage having a small hole extending from said anterior surface to said posterior surface inside said peripheral edge for insertion of instruments for said operation, said small hole being in a position on said bandage to substantially overlie the incision during said operation, and said bandage being transparent.

2. A bandage for maintaining the anterior chamber of an eye according to claim 1, which has a circular or oval shape and a curved section.

3. A bandage for maintaining the anterior chamber of an eye according to claim 1, which comprises a soft material having elasticity.

4. A bandage for maintaining the anterior chamber of an eye according to claim 3, wherein the soft material having elasticity is selected from the group consisting of a hydroxyethyl methacrylate homopolymer, a copolymer comprising hydroxyethyl methacrylate as a monomer component, a copolymer comprising vinyl pyrrolidone as a monomer component, a polyvinyl alcohol type polymer, a silicone rubber and a butyl rubber.

5. A bandage for maintaining the anterior chamber of an eye according to claim 1, wherein the small hole for insertion of instruments for said operation has a shape selected from the group consisting of a circle, a line, a rectangle and a triangle.

6. A bandage for maintaining the anterior chamber of an eye according to claim 1, which has at least one large opening or cut-out.

7. A bandage for maintaining the anterior chamber of an eye according to claim 6, wherein said at least one large opening has a shape selected from the group consisting of a circle, an oval, a trapezoid and a trapezoid-like shape.

8. A bandage for maintaining the anterior chamber of an eye according to claim 6, wherein said at least one cut-out has a fan shape.

9. A method for maintaining the anterior chamber of an eye in an ocular operation, said method comprising the step of placing a bandage as defined in claim 1, in contact with the cornea of an eye.

* * * * *